United States Patent
Bezemer et al.

(10) Patent No.: US 11,622,690 B2
(45) Date of Patent: Apr. 11, 2023

(54) APPROACH FOR MEASURING CAPILLARY REFILL TIME

(71) Applicant: KONINKLIJKE PHILIPS N.V., Eindhoven (NL)

(72) Inventors: Rick Bezemer, Amsterdam (NL); Abigail Acton Flower, Mahopac, NY (US); Cornelis Conradus Adrianus Maria van Zon, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 425 days.

(21) Appl. No.: 15/535,469

(22) PCT Filed: Dec. 14, 2015

(86) PCT No.: PCT/IB2015/059596
§ 371 (c)(1),
(2) Date: Jun. 13, 2017

(87) PCT Pub. No.: WO2016/097979
PCT Pub. Date: Jun. 23, 2016

(65) Prior Publication Data
US 2018/0271382 A1    Sep. 27, 2018

Related U.S. Application Data

(60) Provisional application No. 62/091,654, filed on Dec. 15, 2014.

(51) Int. Cl.
*A61B 5/026* (2006.01)
*A61B 5/02* (2006.01)
*A61B 5/00* (2006.01)

(52) U.S. Cl.
CPC ........ *A61B 5/02007* (2013.01); *A61B 5/0013* (2013.01); *A61B 5/0059* (2013.01);
(Continued)

(58) Field of Classification Search
CPC .............. A61B 5/0261; A61B 5/0059; A61B 2562/0233; A61B 5/6803; A61B 5/02007;
(Continued)

(56) References Cited

U.S. PATENT DOCUMENTS 7,483,733 B2    1/2009  Shani et al.
8,179,604 B1    5/2012  Prada Gomez et al.
(Continued)

FOREIGN PATENT DOCUMENTS

JP    2013192651 A    9/2013
RU    2353410 C2    4/2009
(Continued)

OTHER PUBLICATIONS

W. Karlen et al., Capillary Refill Time Assessment Using a Mobile Phone Application (iRefill), American Society of Anethesiologists Annual Meeting, Oct. 17, 2010, pp. 1-2, American Society of Anesthesiologists, San Diego, United States (Year: 2010).*
(Continued)

*Primary Examiner* — Bill Thomson
*Assistant Examiner* — Aminah Asghar (57) ABSTRACT

The capillary refill time (CRT) of a patient is an important feature in the determination of cardiovascular system health. Quick re-perfusion of the microcirculation (namely, the capillaries) is a good indication that the cardiovascular system is able to efficiently distribute blood throughout the body. Current systems use unreliable or subjective methods to test the CRT. Additionally, the calculation of CRT is not generally used in the adult medical space as it is more commonly used in pediatrics. The present application describes a system and method for calculating a patient's CRT using a mobile device with an integrated camera and light source, or an optical head-mounted display using a light source in combination with ambient light to calculate (Continued)

the CRT. Once a patient's CRT is calculated, an integrated application classifies the data and sends it to the treating clinician for review.

11 Claims, 6 Drawing Sheets

(52) U.S. Cl.
CPC ........ *A61B 5/02028* (2013.01); *A61B 5/0261* (2013.01); *A61B 5/6803* (2013.01); *A61B 5/6826* (2013.01); *A61B 5/6898* (2013.01); *A61B 5/7445* (2013.01); *A61B 2562/0233* (2013.01)

(58) Field of Classification Search
CPC . A61B 5/6826; A61B 5/02028; A61B 5/0013; A61B 5/7445; A61B 5/6898; A61B 5/0077

See application file for complete search history.

(56) References Cited

U.S. PATENT DOCUMENTS

| | | | |
|---|---|---|---|
| 2002/0115935 A1* | 8/2002 | Shani ................ | A61B 5/0059 600/549 |
| 2007/0282182 A1 | 12/2007 | Messerges et al. | |
| 2007/0299322 A1* | 12/2007 | Miyajima ........... | A61B 5/0008 600/301 |
| 2009/0105556 A1 | 4/2009 | Fricke et al. | |
| 2009/0143655 A1* | 6/2009 | Shani ................ | A61B 5/0059 600/323 |
| 2009/0203998 A1 | 8/2009 | Klinghult et al. | |
| 2012/0130211 A1 | 5/2012 | Kobayashi et al. | |
| 2013/0018241 A1* | 1/2013 | Bezzerides ........ | A61B 5/14552 600/324 |
| 2013/0072145 A1 | 3/2013 | Dantu | |
| 2013/0245396 A1 | 9/2013 | Berman et al. | |
| 2013/0253332 A1* | 9/2013 | Hayman ............. | A61B 5/0059 600/476 |
| 2014/0018647 A1 | 1/2014 | Segman | |
| 2014/0039309 A1* | 2/2014 | Harris ............... | A61M 5/16836 600/431 |
| 2015/0031965 A1* | 1/2015 | Visvanathan ........ | A61B 5/0059 600/301 |
| 2015/0148623 A1* | 5/2015 | Benaron ............. | A61B 5/0059 600/306 |
| 2016/0038048 A1 | 2/2016 | Ting et al. | |
| 2017/0014075 A1* | 1/2017 | Morimura .......... | A61B 5/02241 |
| 2017/0290519 A1* | 10/2017 | Zhou .................... | G16H 40/67 |

FOREIGN PATENT DOCUMENTS

| | | |
|---|---|---|
| WO | 0106926 A1 | 2/2001 |
| WO | 2007086071 A2 | 8/2007 |
| WO | 2009053920 A1 | 4/2009 |

OTHER PUBLICATIONS

Dallas M., "The future of healthcare—We have the technology—Google Glass could revolutionise veterinary and medical practice", Social Vet Professionals, http://www.linkedin.com/groups/future-healthcare-We-have-technology-4810470.S.225743011 (Abstract).

Shavit et al., "A Novel Imaging Technique to Measure Capillary-Refill Time: Improving Diagnostic Accuracy for Dehydration in Young Children With Gastroenteritis", Official Journal of the American Academy of Pediatrics, Pediatrics, vol. 118, No. 6, Dec. 2006, pp. 2402-2409.

Spigulis, "Biophotonic Technologies for Non-Invasive Assessment of Skin Condition and Blood Microcirculation", Biophotonics, Latvian Journal of Physics and Technical Sciences, 2012, No. 5, pp. 63-80.

* cited by examiner

APPROACH FOR MEASURING CAPILLARY REFILL TIME

CROSS-REFERENCE TO PRIOR APPLICATIONS

This application is the U.S. National Phase application under 35 U.S.C. § 371 of International Application No. PCT/IB2015/059596, filed on Dec. 14, 2015, which claims the benefit of U.S. Provisional Application Ser. No. 62/091,654, filed Dec. 15, 2014. These applications are hereby incorporated by reference herein, for all purposes.

FIELD

The following relates generally to measurement of the capillary refill time. It finds particular application in conjunction with providing accurate subject specific capillary refill times for both pediatric subjects and adult subjects in testing and diagnosing dehydration or profusion-acute hypotension. It also finds particular application in conjunction with providing these subject specific calculations to a clinician based upon standardized inputs. However, it is to be understood that the following also finds application in other usage scenarios and is not necessarily limited to the aforementioned applications.

BACKGROUND

Capillary refill time (CRT) of a subject is a useful metric in assessing cardiovascular system health. Quick re-perfusion of the microcirculation (e.g. in the capillaries) is a good indication that the cardiovascular system is able to efficiently distribute blood throughout the body, whereas slow re-perfusion may indicate a cardiovascular problem calling for investigation. Current methods of assessing CRT employ subjective measurement made by the attending clinician, called a "finger blanch test." In this test, the clinician squeezes the subject's finger, releases, and counts the number of seconds needed for the finger to regain its pinkish color a subjective and infrequently recorded measure. The finger blanch test is also relative as one clinician may press the subject's finger harder than another clinician.

Determining the exact time when a finger, subjected to a finger blanch test, returns to its starting color is subjective and has proven to be a difficult task to apply uniformly. Determining exactly when tissue color has returned to baseline color and counting the time accurately for a 2- or 3-second threshold is a difficult task which limits the clinical value of the test.

SUMMARY

The following also provides new and improved methods and systems which overcome the above-referenced problems and others.

In accordance with one aspect, a method for measuring CRT is disclosed. The method comprises, emitting a light from a light source and turning on a camera located near the light source to identify a patient's finger. A patient's finger is then pressed for a determined amount of time. An integrated application on a mobile device is started wherein the integrated application turns on the light source and uses the camera, which is located near the light source, to detect color changes in the patient's finger and using this information, the method calculates the CRT from the time elapsed between the change in the color of the patient's finger.

In accordance with another aspect of the present application, an apparatus for measuring CRT is disclosed comprising, a light source for emitting light and a camera near the light source configured to identify a patient's finger. Using at least one patient finger and at least one processor configured to turn on the light source and camera, the processor further configured to use the camera to detect color changes in the patient's finger to calculate the CRT from the time elapsed between the change in the color of the patient's finger.

In accordance with another aspect of the present application, a system for measuring and calculating CRT is disclosed. The system comprises one or more processors configured to calculate CRT for a patient using a camera and light source to determine time elapsed between a change in color of a patient's finger from a starting position and an ending position. The system also includes memory configured to store patient data, a communication network configured to send and receive clinical information, and a user interface configured to receive inputs from the at least one processor and memory, the user interface configured to display the calculated result.

One advantage resides in improved determination and calculation of a subject's CRT based upon objective testing criteria.

Another advantage resides in improved clinical workflow.

Another advantage resides in improved patient care.

Still further advantages of the present invention will be appreciated to those of ordinary skill in the art upon reading and understanding the following detailed description.

BRIEF DESCRIPTION OF THE DRAWINGS

The invention may take form in various components and arrangements of components, and in various steps and arrangement of steps. The drawings are only for purposes of illustrating the preferred embodiments and are not to be construed as limiting the invention.

DETAILED DESCRIPTION

Disclosed herein are apparatuses and methods which determine a patient's capillary refill time (CRT) using objective techniques. (More generally, the disclosed CRT measurement techniques can be applied to a subject, who may be a patient, or a subject undergoing a routine physical examination or clinical screening, or so forth for simplicity, the term "patient" is used herein). In one approach, using a readily available camera, embedded light source (camera flash), and an integrated application (i.e., electronic data processing device), a patient's finger is squeezed or pressed, and, using the LED wavelength scale on the camera color scale, it is determined how long it takes the patient's finger to return to its starting color before it was pressed. The CRT may be assessed using automatic evaluation of the color return. In an automatic approach, a flexible non-transparent cuff is provided that squeezes a patient's finger using a standardized and predetermined force. Upon release, the camera determines how long until the patient's finger returns to its stating color. This information is then transmitted to a user interface either on a mobile device or a separate medical device.

Disclosed herein are approaches for calculating the CRT of a patient. Upon completion of the calculation, the CRT is, in some embodiments, classified into a classification category and the results and classification are submitted to the clinician for review. In the case of an adult patient, CRT is typically used to test for dehydration or acute hypertension. CRT is typically used in the pediatrics space for checking dehydration in infants and children.

Figure 1:
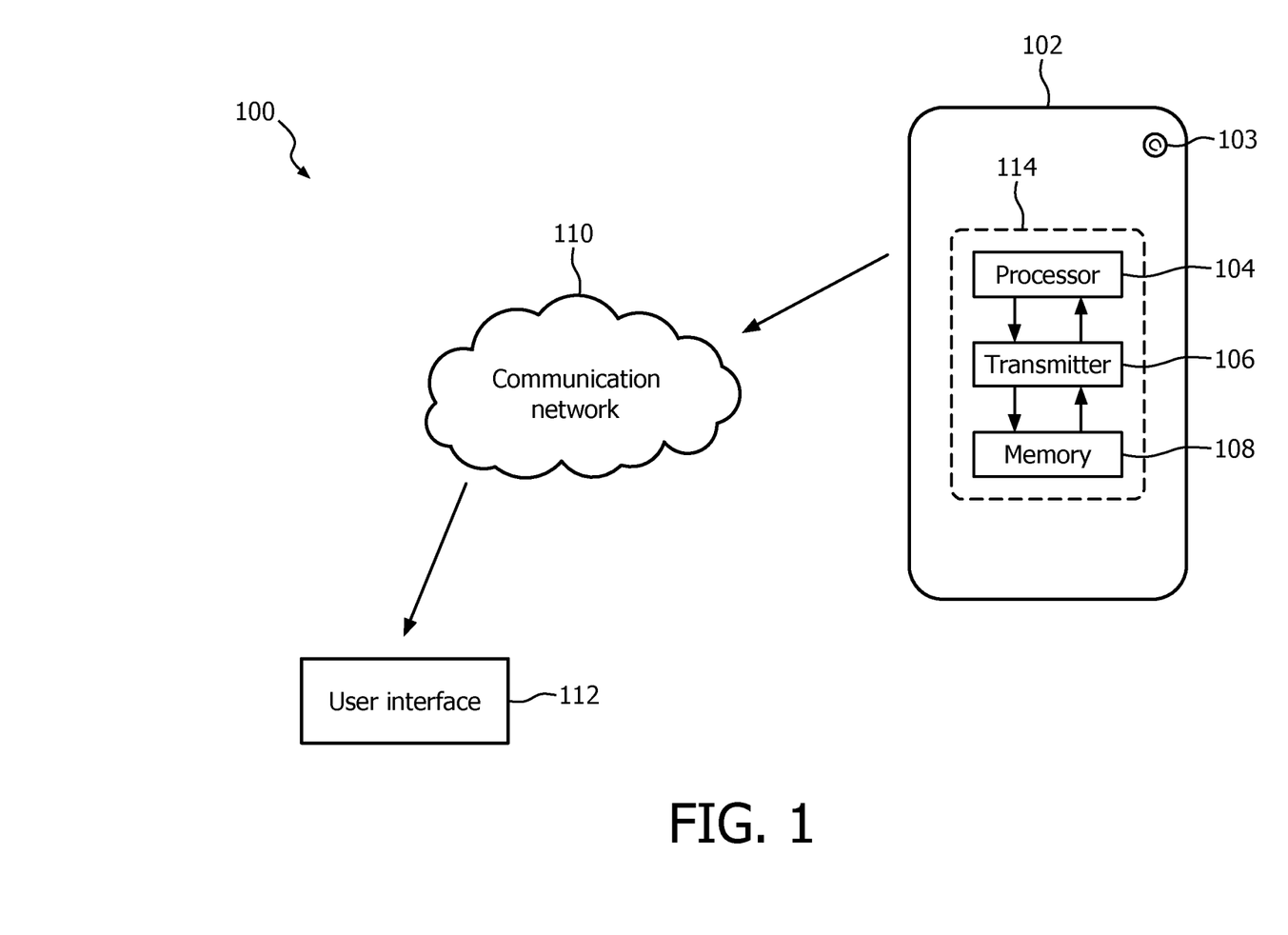
FIG. 1 illustrates a representative system embodying the method and apparatus for calculating the capillary refill time.

With reference to FIG. 1, a block diagram illustrating a representative system for calculating capillary refill time (CRT) and sending it to a user interface for a clinician to review is shown. The system 100 suitably includes a mobile or wearable device 102 equipped with a camera 103 that acquires images or optical data for the finger over a capillary refill time interval, at least one electronic processor 104 (for example, a microprocessor, a microcontroller, or the like) that computes the capillary refill time (CRT) from the acquired images or optical data, an optional transmitter 106 for transmitting calculated patient information off the mobile or wearable device 102, and memory 108 for storing calculated patient data. In some embodiments, a user interface 112 (for example, a multi-function patient monitor, a nurses' station computer, or so forth) is interconnected via a communications network 110 to receive the CRT value transmitted from the mobile device 102. Additionally or alternatively, the device 102 may display the CRT value on a display screen 114 of the device 102 without transmitting it (note that the electronic components 104, 106, 108 are typically disposed inside the mobile or wearable device 102, so that they are occluded by the display screen 114), and the value is suitably read and entered into the patient record manually by the doctor, nurse, or other medical professional acquiring the CRT. It is contemplated that the communications network 110 includes one or more of the Internet, an Intranet, a local area network, a wide area network, a wireless network, a wired network, a cellular network, a data bus, a Bluetooth, infrared, or other short-range wireless connection, and the like. It should also be appreciated that the components of the system may be located at a central location or at multiple remote locations.

The one or more processors 104 suitably execute computer executable instructions embodying the foregoing functionality and controlling the camera 103 to acquire the images or optical data, where the computer executable instructions are stored on the memory 108 associated with the processors 104. It is, however, contemplated that at least some of the foregoing functionality is implemented in hardware without the use of processors. For example, analog circuitry can be employed to implement some of the operational/control functions of the camera 103. Further, the components of the system 100 optionally include transmitter units 106 providing the processors 104 an interface from which to communicate over the communications network 110 and provide the information to the physician over the user interface 112.

Figure 2A:
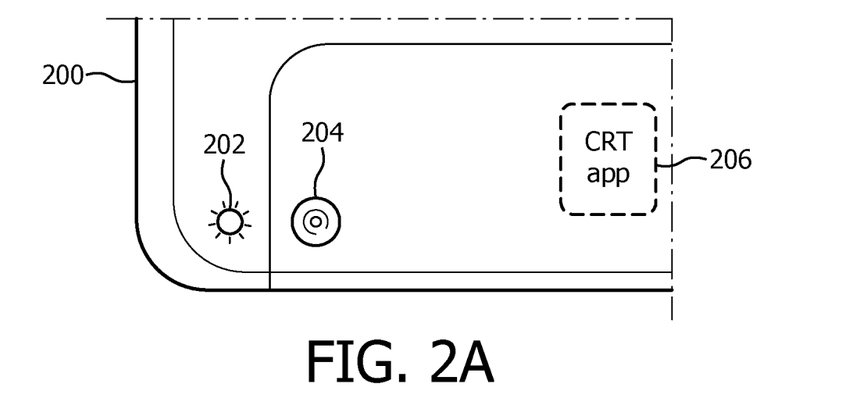
FIG. 2a illustrates an example capillary refill test (CRT) apparatus with a camera lens and an integrated light source offset from the camera lens for capturing and calculating a subject's capillary refill time.

With reference to FIG. 2(a), in one illustrative embodiment the mobile device 102 of FIG. 1 comprises a camera-equipped mobile device 200 (for example, a camera-equipped cellular telephone, a camera-equipped tablet computer, or so forth) with an integrated light source (e.g., an LED) 202, the integrated light source being conventionally used as a flash light for still picture photography, or as a torch light for sustained illumination, e.g., for taking videos, and a camera 204. In general, the camera 204 includes a charge-coupled device (CCD), CMOS or other image sensor array optically coupled with a lens (which could be a pinhole lens, although typically a refractive lens element such as a compound lens is provided). In some embodiments, the camera 204 may be configured to provide adjustable focus. The camera-equipped mobile device 200 is configured by suitable firmware or software to operate the light source 202 and camera 204 to acquire photographs of people, places, objects, or so forth. For example, the camera may be a "point-and-shoot" camera. As disclosed herein, the camera is additionally configured, for example by way of a suitable application program ("app") 206 (diagrammatically indicated in FIG. 2(a)) executing on the mobile device 102, to perform capillary refill time (CRT) measurement using the camera 204 and light source 202. For example, the mobile device 200 may be running the iOS mobile operating system (available from Apple Corp. Cupertino, Calif., USA) and the CRT app 206 is an iOS app. In another embodiment, the mobile device 200 runs the Android mobile operating system and the CRT app 206 is an Android app.

Figure 2B:
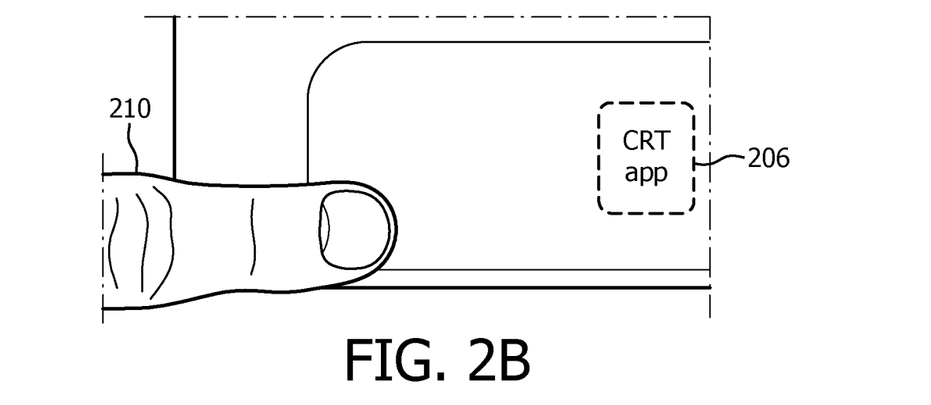
FIG. 2b illustrates an exemplary use of the CRT apparatus of FIG. 1 with a subject's finger to calculate the capillary refill time.

With reference to FIG. 2(b), to measure capillary refill time, a clinician would start the CRT app 206, for example by touching an icon representing the CRT app 206 shown on a display of the mobile device 200. (The display is on the opposite side of the mobile device 200 and hence is not visible in the views of FIGS. 2(a) and 2(b)). The CRT app 206 then prompts the user (for example, via text shown on the display and/or via a simulated voice message) to place one of the patient's fingers 210 over both the camera 204 and the integrated light source 202, and hold it there for a few seconds without pressing. After a few seconds, the clinician is prompted by the CRT app 206 to press or squeeze the patient's finger 210 onto the camera 204 for a few seconds, and then to release the pressure on the patient's finger while holding the patient's finger 210 there for another few seconds. (In an alternative embodiment, the CRT app 206 does not prompt the clinician to press or squeeze the finger but instead monitors the output of the camera 204 to detect this operation automatically based on optically detected blanching of the finger.) In conjunction with the test, the CRT app 206 operates the integrated light source 202 to cause the light source 202 to generate light that illuminates the finger 210 at least proximate to the point where the finger is pressing against the camera 204. It will be noted that the light source 202 is laterally offset from the camera 204, so that the light source 202 does not directly illuminate the point where the finger is pressing against the camera 204. However, the inventors have found that a typical human finger is sufficiently translucent that a sufficient amount of light "leaks" from the light source 202 into the field-of-view of the camera 204 to provide illumination for the CRT measurement. The CRT app 206 calculates the patient's CRT by analyzing the camera image stream generated by the camera 204. In one approach, the CRT analysis makes use of the Red and/or Green and/or Blue component of the image stream, and looks for signal distortions (e.g. color changes) that identify the onset of squeezing, a second distortion that identifies the release, and, finally, the return of the signals to their pre-squeeze characteristics. The CRT can be derived from the time elapsed between the latter two events.

In some mobile operating systems, low-level access to the camera may be unavailable. In such cases, the detection of the onset of finger pressure, release of the finger pressure, and measurement of the color return is suitably based on a time series of "images" acquired by the camera. For example, in video mode the camera acquires a time series of images (frames), typically at a rate of 30 frames (images) per second, which is fast enough for good CRT temporal resolution. Since the finger 10 is pressed against the camera 204, the acquired "images" are not actually in-focus; however, the integrated intensity per frame (for example, computed as the average pixel intensity per frame) is a suitable metric for the skin color and can be used to characterize the color return.

Figure 2C:
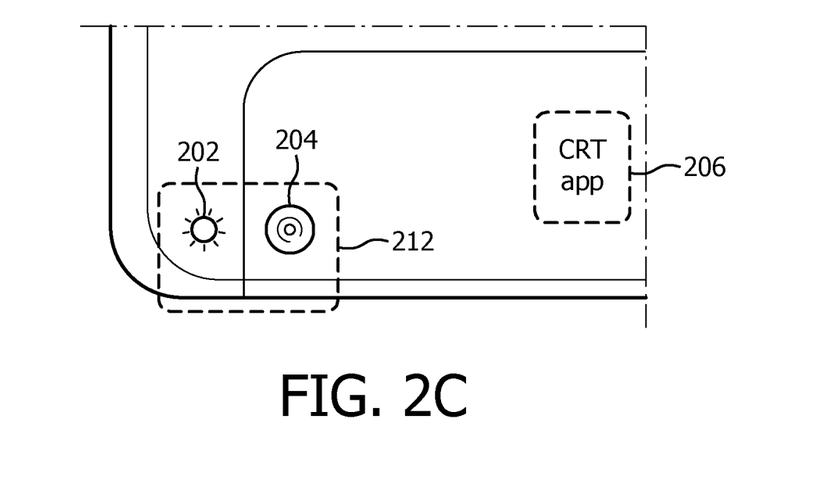
FIG. 2c illustrates a CRT apparatus for capturing and calculating a subject's capillary refill time with a cuff for blocking ambient light from reaching a subject's finger and optionally for applying uniform pressure to the subject's finger during the test.
Figure 6:
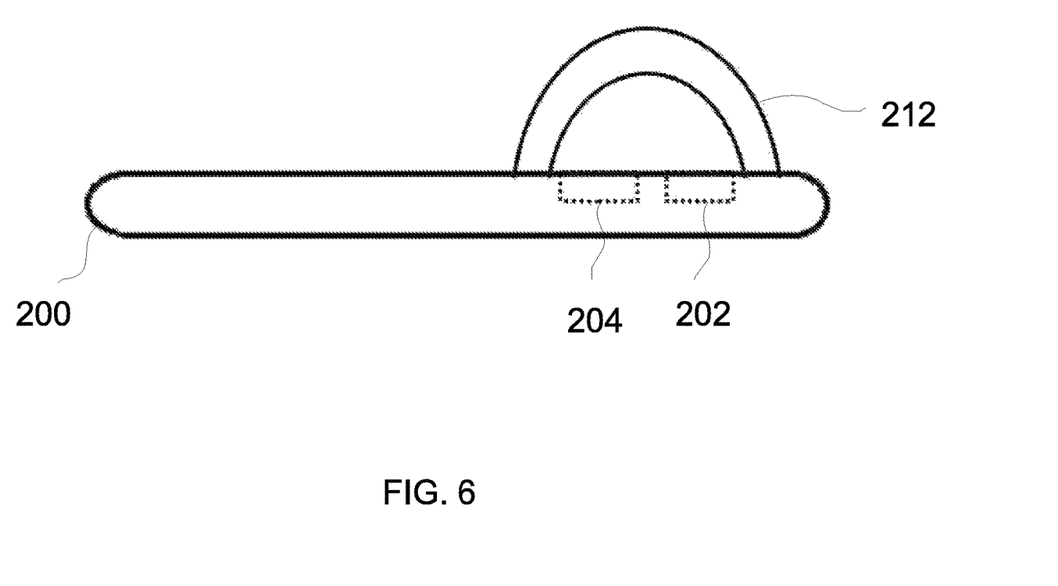
FIG. 6 illustrates the cuff clipped over the light source and the camera of the mobile device.

With reference to FIG. 2(c), in a variant embodiment, a patient's CRT is calculated using the hardware described with reference to FIG. 2(a) and further including a cuff 212 (shown in dashed outline form in FIG. 2(c)) that is clipped over the light source 202 and the camera 204 of the mobile device 200 prior to the CRT measurement, as also shown in FIG. 6. The patient slips his or her finger into the cuff 212, which shields it from environmental light during the measurement. In one embodiment, the cuff 212 is a passive cuff that is non-transparent and flexible, the latter in order to allow the clinician to squeeze the finger while in the cuff. The passive cuff provides finger alignment, and may include a soft material to cushion and distribute the applied pressure on the finger.

In another embodiment, the cuff 212 is a rigid or inflatable cuff that also serves as a mechanical device for applying pressure to the finger. In this approach, a patient's CRT is calculated using the rigid or inflatable cuff 212 for shielding the finger from environmental light during CRT measurement. In a rigid cuff embodiment, the cuff includes one or more built-in servos motors (not shown) that perform the squeeze-and-release actions, allowing for standardized pressures. In an inflatable cuff embodiment the cuff is inflatable, for example using a diaphragm pump built into the cuff, to apply the pressure to the finger in the inflated state. In either a rigid or inflatable embodiment, pressure sensors (not shown) are optionally included to provide positive feedback regarding the applied pressure. Advantageously, servo motors of the rigid cuff 212 (or the inflation unit of an inflatable cuff) are controlled by the CRT app 206 allowing the app 206 to know the exact release time.

Although the cuff 212 is described as non-transparent or opaque, this is not necessarily required. Ambient light is problematic insofar as it may include transients that can interfere with the capillary refill monitoring, or may be so bright as to reduce sensitivity of the capillary refill monitoring. Typically ambient light intensity is essentially constant in a doctor's office or hospital over the time frame of the CRT measurement, so cuff opacity may not be essential, or a translucent cuff may be sufficient. Even if the cuff 212 is not designed to block ambient light, it may be useful to guide the patient's finger into the proper position for the CRT measurement, and as already described in some embodiments the cuff 212 also provides the active pressure for the CRT measurement.

Figure 3:
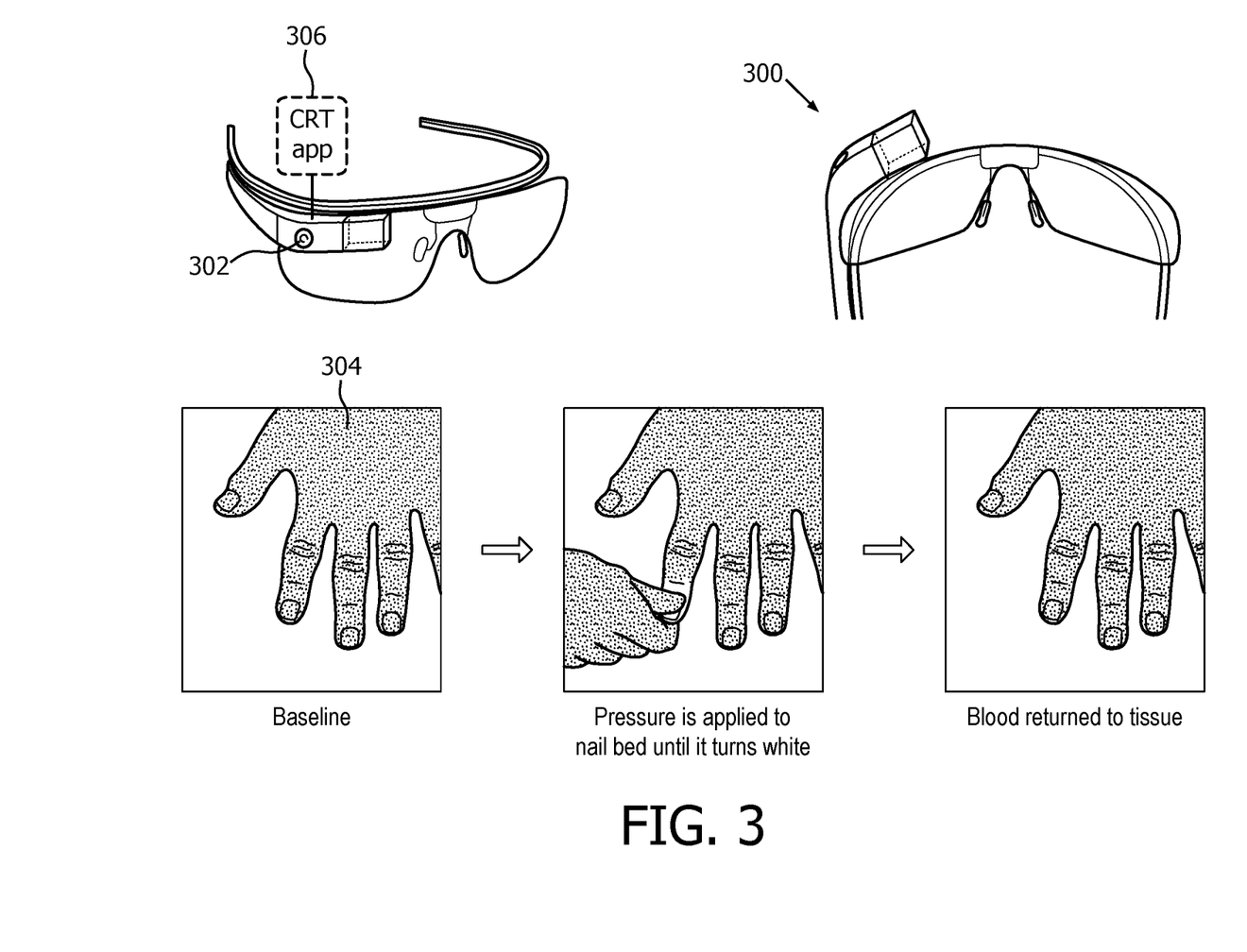
FIG. 3 illustrates another example CRT apparatus for use in calculating capillary refill time.

With reference to FIG. 3, in another illustrative embodiment the device 102 of FIG. 1 is a wearable device, such as an illustrative optical head-mounted display (OHMD) 300 having the form of eyeglasses (i.e. spectacles). The OHMD 300 includes a camera 302, and the display of the OHMD 300 serves as a monitor for feedback. The device 300 further includes a microprocessor or microcontroller running an application program ("app") 306 to perform the capillary refill time (CRT) measurement. In one contemplated embodiment, the OHMD 300 is a Google Glass unit (available from Google, Mountain View, Calif., USA) running an application program ("app") 306 under a Google Glasses-specific version of the Android mobile operating system. To perform a CRT measurement, the clinician wears the OHMD 300 and views the hand 304 of the patient whereby the camera 302 is focused on the hand 304. The CRT measurement may be initiated in various ways, such as by an instruction provided to the clinician via the display of the OHMD 300 or via a simulated voice generated by the OHMD unit 300, or by a verbal command spoken by the clinician and detected by a voice recognition component of the OHMD 300, or by automatic detection of the hand 304 in the field-of-view of the camera 304 identified using suitable image segmentation techniques, or so forth. The camera 302 detects the fingernail of interest (or alternatively views the finger pad side of the finger), performs a baseline color assessment, and provides a baseline color index (e.g. peak intensity or AUC of the finger nail intensity histogram of the red channel). Then, the clinician applies pressure to the finger nail of interest for a few seconds. When the physician releases the finger, the camera 302 re-detects the finger and records its color in each video frame, for example, over ten seconds at 30 frames/sec. The camera 302 can capture the color changes in the patient's finger using video recording or a time sequence of still images (i.e. photographs) to be analyzed. After completion of the recording, the CRT is determined by determining the video frame or still photo where the finger nail regained its baseline color, or by fitting a mathematical function to the measured color in the sequential video frames for more reproducible determination of the capillary refill time.

It will be noted that the embodiment of FIG. 3 differs from the embodiments of FIGS. 2(a), (b), (c) in that there is no analog to the camera light source 202. The embodiment of FIG. 3 relies on ambient light in order to acquire images of the fingernail. Additionally or alternatively, it is contemplated to include a light source or other light source on the OHMD 300.

Figure 4:
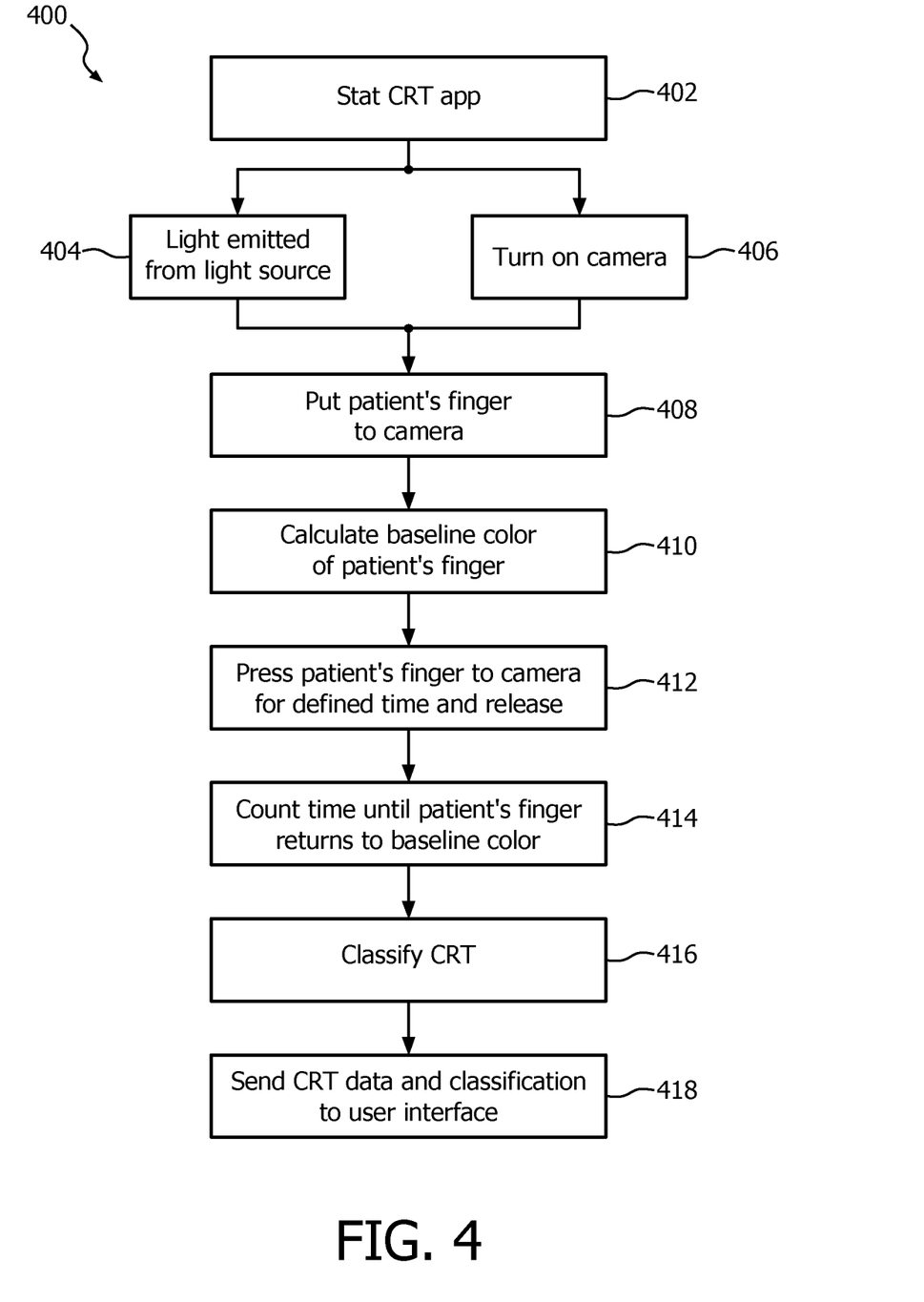
FIG. 4 illustrates a method for calculating the capillary refill time.

With reference to FIG. 4 a process flowchart is shown diagramming an illustrative method 400 for measuring a patient's capillary refill time. The method 400 is suitable for devices, such as the camera-equipped device 200 of FIGS. 2(a), 2(b), 2(c), that have a camera and light source that are close enough to cover with a single finger digit. In an operation 402, the CRT app 206 is started on the mobile device 200. The CRT app 206 turns on the light source 202 in an operation 404 and activates the camera 204 in an operation 406. In an operation 408, the patient's finger is pressed to the camera, and the camera calculates the baseline color of the patient's finger in an operation 410. The baseline color is the starting point from which the camera will detect the patient's capillary refill time. After baseline measurement operation 410, a clinician (or the automatic cuff 212 in embodiments including same) squeezes or presses (i.e.

applies pressure to) the patient's finger for a defined amount of time in an operation 412. For example, the patient's finger is pressed for 3 seconds in some suitable embodiments. At the end of the operation 412, the clinician or the automatic cuff then releases the patient's finger. In an operation 414 the camera takes video images (frames) or a time series of still images of the patient's finger as the capillaries refill with blood, and the CRT app 206 calculates the patient's CRT as the amount of time elapsed until the patient's finger returns to its baseline color after being squeezed. Optionally, in an operation 416 the CRT app 206 classifies the data into a classification group for the clinician. For example, the classification groups could be classified as 'very low' (e.g. CRT<1 sec), 'low' (e.g. CRT=1-2 sec), 'normal' (e.g. CRT=2-3 sec), 'high' (e.g. CRT=3-4 sec), or 'very high' (e.g. CRT>4 sec). In an operation 418, the CRT value and/or the optional CRT classification information is sent to the user interface for the clinician to review.

CRT measurement using the OHMD 300 of FIG. 3 can be similarly performed. Here there is no analog to the operation 404, and the operation 408 corresponds to focusing the camera 302 onto the fingernail, for example by having the clinician wearing the OHMD 300 look at the fingernail. An image segmentation algorithm may optionally be applied to more particularly identify the fingernail region in the image.

Figure 5:
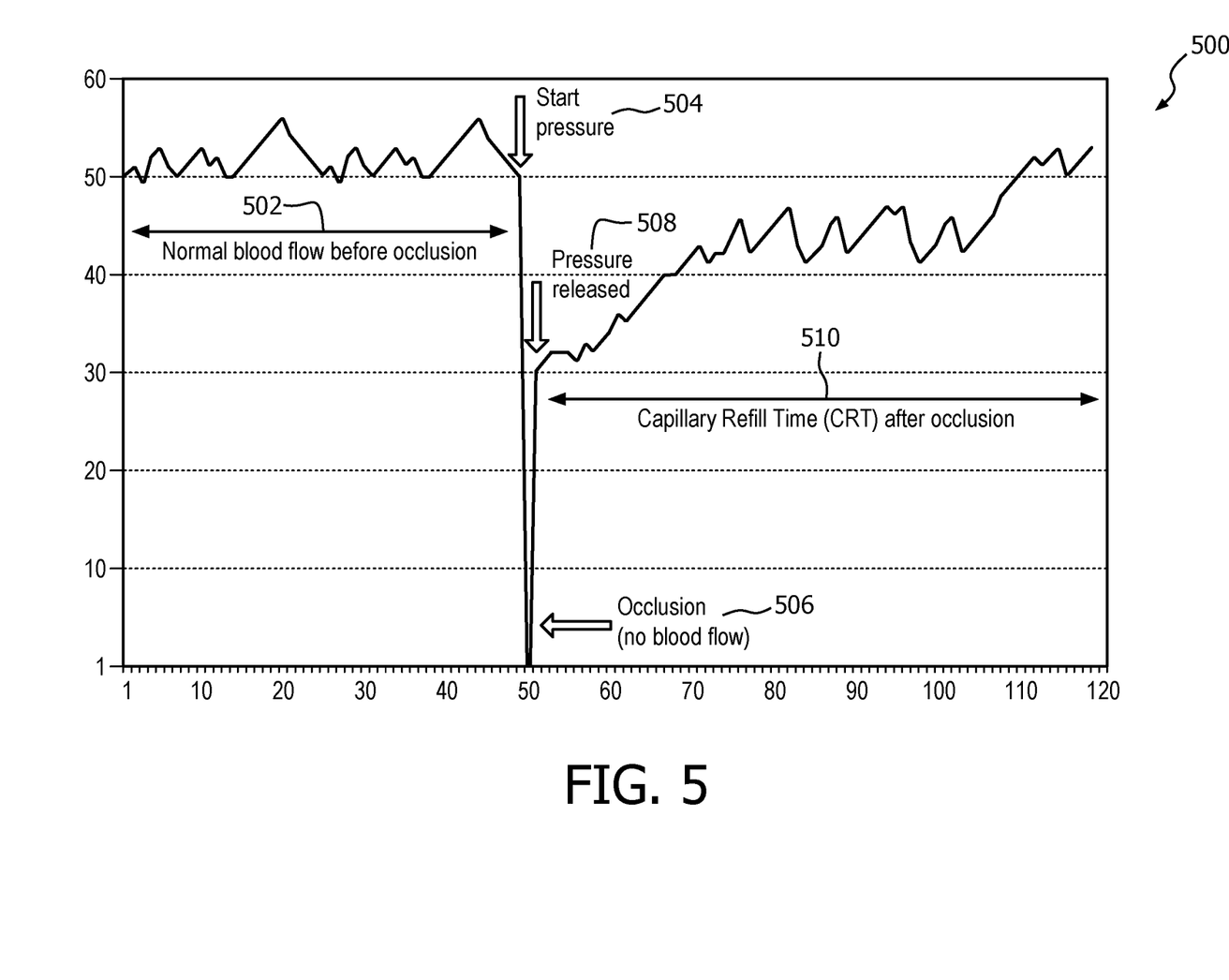
FIG. 5 illustrates an example diagram calculating the CRT wherein the blood flow is normal, then is occluded, and finally returning to normal.

With reference to FIG. 5 an illustrative example of the optical signal acquired by the camera 204 of the mobile device 200, or by the camera 302 of the OHMD 300, during the CRT measurement is shown. This diagram is generated by the CRT app 206, 306, and may in some embodiments be displayed for the clinician on the user interface. A region 502 of the diagram indicates the baseline optical signal before any pressure is applied 502. When pressure is applied (indicated by arrow 504), the optical signal undergoes a rapid transient 504. The nature of this transient depends upon the specific arrangement of the camera, illumination, and source of pressure. FIG. 5 shows the transient 504 as a sharp decrease in signal, which may occur because the clinician's hand applying the pressure occludes view of the fingernail. On the other hand, for the embodiment of FIGS. 2(a), 2(b), 2(c) the transient may be different since the view of the camera 204 is never occluded. When the pressure from either the clinician or the pressure cuff is released, a further transient 508 may be observed. Thereafter, as the capillaries refill with blood, the camera captures the corresponding color change and the time is recorded in the integrated application 410. When the color returns to the baseline color, the integrated application stops recording and calculates the CRT.

It will be appreciated that the capillary refill time (CRT) may be quantified in various ways. In one approach, the CRT is taken as the time at which the rising signal in region 510 returns to the baseline signal level observed in the region 502. However, this approach can be prone to some error for example, in some cases, it has been observed that the signal may briefly overshoot or undershoot the baseline. Improved accuracy can be obtained by characterizing the shape of the recovery curve in the region 510, for example by determining a time constant assuming an exponential shape in the recovery region 510. Another approach is to take the CRT as the 90% recovery time (or some other designated point), that is, the time for the optical signal to reach 90% of the baseline value, which can reduce the impact of overshoot or undershoot on the accuracy of the CRT measurement.

The CRT measurement process also includes determining the "start" time, that is, the time at which the pressure applied to the finger is removed. This can be done in various ways. In prospective approaches, a control signal is provided in real-time to indicate removal of the pressure. For example, in embodiments in accord with FIG. 2(c) that include an actuated cuff 212, the control signal suitably corresponds to removal of the applied pressure by the cuff 212. In manual pressure approaches, a prospective start time can be taken as a time that the physician is instructed to release the pressure, but this assumes the physician promptly does so. In retrospective approaches, a time series of images/frames, or a camera channel (e.g. red, green, or blue channel) signal measured as a function of time, is acquired over a time interval sufficient to encompass the capillary refill time interval. For example, start of the acquisition of the video stream may be triggered by a signal to the clinician to begin the CRT test, and the video stream may be stopped after a fixed time interval of several seconds to tens of seconds or by a stopping criterion applied to the measured images/frames/signal. In these retrospective approaches, signal processing is applied to detect the release of pressure corresponding to the "start" time. To illustrate, in the example of FIG. 5 the "start" time can be detected by detecting the signal loss during occlusion 506 followed by the (near instantaneous) signal jump when the occlusion is removed—the latter is a suitable definition of the "start" time.

The optical signal that is monitored to assess the capillary refill process can also be variously chosen. As some illustrative examples, the optical signal may be a color value (e.g., measured using suitable color coordinates in CIE coordinate space or another color space), a tint or shade value, an intensity value (for a particular color channel or for the measured light without any spectral decomposition), or so forth.

In the illustrative embodiments, the CRT is measured for a finger, and conventionally CRT is measured for a finger. However, it is also contemplated to employ the disclosed CRT measurement devices to measure capillary recovery time for skin in other anatomical regions, such as the earlobe or forearm. In general, the CRT measurement entails applying pressure to the skin of the finger (or earlobe, or forearm, et cetera) to blanch the skin at the point of pressure, and then optically measuring the capillary recovery time for the skin at the point of pressure upon removal of that pressure.

The invention has been described with reference to the preferred embodiments. Modifications and alterations may occur to others upon reading and understanding the preceding detailed description. It is intended that the invention be constructed as including all such modifications and alterations insofar as they come within the scope of the appended claims or the equivalents thereof.

The invention claimed is:

1. A capillary refill time (CRT) measurement device operative to measure CRT for a finger upon release of pressure applied to the finger, the CRT measurement device comprising:

a mobile device including a camera and a camera light source configured to emit light toward the finger, wherein at least some of the light emitted by the camera light source is configured to reach a field-of-view of the camera;

a display component;

a cuff removably clipped to the mobile device over the camera, the cuff comprising a camera shielding portion shielding the finger and the camera from environmental light, wherein the cuff further comprises one or more built-in servo motors that, when activated, apply standardized pressure to the finger; and an electronic processor programmed by an integrated CRT application to perform a CRT measurement by operations including:

controlling the one or more built-in servo motors, determining a time at which the pressure applied to the finger is released to begin the CRT measurement based on a control signal, wherein the control signal corresponds to a removal of the applied pressure by the one or more built-in servo motors;

operating the camera to measure an optical signal from the finger over a time interval encompassing the CRT beginning at the time at which the pressure applied to the finger is released, determining a CRT value based on analysis of the measured optical signal, and displaying the determined CRT value on the display component.

2. The CRT measurement device of claim 1, wherein the mobile device comprises a cellphone.

3. The CRT measurement device of claim 1, wherein the camera light source is offset laterally from the camera and operating the camera includes operating the camera light source to illuminate the finger at least during the time interval encompassing the CRT.

4. The CRT measurement device of claim 1, wherein operating the camera comprises operating the camera to acquire video or a time sequence of still images of the finger, and the determining comprises determining the CRT value based on the acquired video or time sequence of still images.

5. The CRT measurement device of claim 1, wherein the operation of determining the CRT value based on analysis of the measured optical signal uses a red and/or green and/or blue component of a camera image stream generated by the operation of operating the camera to detect signal distortions to calculate the CRT value.

6. The CRT measurement device of claim 1, wherein the camera and the camera light source are arranged side-by-side on an outer surface of the mobile device.

7. A method for measuring capillary refill time (CRT) for a finger upon release of pressure applied to the finger, the method comprising:

providing a mobile device comprising a camera and a camera light source configured to emit light toward the finger, wherein the camera and the camera light source are arranged side-by-side on an outer surface of the mobile device, the mobile device further comprising a display component;

clipping a removable cuff to the mobile device over the camera, the cuff comprising a camera shielding portion shielding the camera and the finger from environmental light, wherein the cuff further comprises one or more built-in servo motors that, when activated, apply standardized pressure to the finger;

activating the built-in servo motors to apply the standardized pressure to the finger inserted into the removable cuff;

operating the camera light source to illuminate the finger at least proximate to the point where the finger is pressing against the camera, wherein at least some of the light emitted from the camera light source reaches a field-of-view of the camera;

measuring an optical signal using the mobile device, wherein the optical signal is measured over a time interval encompassing a measurement associated with the finger;

calculating the CRT based on analysis of the measured optical signal; and displaying the CRT on the display component.

8. The method according to claim 7, wherein the mobile device uses at least one of a red, green, and blue component of a camera image stream to determine color changes in the finger.

9. The method according to claim 7, wherein the camera light source is offset laterally from the camera and wherein the measurement of the optical signal from the finger using the camera further includes illuminating the finger during the measurement using the camera light source.

10. The method according to claim 7, wherein the optical signal is measured by acquiring video images or still images of the finger using the camera and the CRT is calculated by analyzing the video images or still images of the finger and wherein the CRT is calculated as an amount of time elapsed until the finger returns to its baseline color after being pressed or squeezed.

11. The method according to claim 7, wherein the mobile device classifies the CRT into a classification group as 'very low', 'low', 'normal', 'high', or 'very high'.

* * * * *